United States Patent
Liu et al.

(10) Patent No.: US 10,369,197 B2
(45) Date of Patent: Aug. 6, 2019

(54) USE OF CD24 FOR LOWERING LOW-DENSITY LIPOPROTEIN CHOLESTEROL LEVELS

(71) Applicant: OncoImmune, Inc., Rockville, MD (US)

(72) Inventors: Yang Liu, Washington, DC (US); Pan Zheng, Washington, DC (US)

(73) Assignee: OncoImmune, Inc., Rockville, MD (US)

( * ) Notice: Subject to any disclaimer, the term of this patent is extended or adjusted under 35 U.S.C. 154(b) by 0 days.

(21) Appl. No.: 15/572,330

(22) PCT Filed: May 6, 2016

(86) PCT No.: PCT/US2016/031109
§ 371 (c)(1),
(2) Date: Nov. 7, 2017

(87) PCT Pub. No.: WO2016/179456
PCT Pub. Date: Nov. 10, 2016

(65) Prior Publication Data
US 2018/0110828 A1    Apr. 26, 2018

Related U.S. Application Data

(60) Provisional application No. 62/158,157, filed on May 7, 2015.

(51) Int. Cl.
| | | |
|---|---|---|
| *C07K 14/705* | (2006.01) | |
| *C07K 16/46* | (2006.01) | |
| *A61K 38/17* | (2006.01) | |
| *G01N 33/92* | (2006.01) | |
| *A61P 9/10* | (2006.01) | |
| *G01N 33/50* | (2006.01) | |

(52) U.S. Cl.
CPC ............ *A61K 38/177* (2013.01); *A61P 9/10* (2018.01); *C07K 14/70596* (2013.01); *G01N 33/502* (2013.01); *G01N 33/92* (2013.01); *C07K 2319/30* (2013.01); *G01N 2333/70596* (2013.01); *G01N 2800/323* (2013.01)

(58) Field of Classification Search
CPC ... A61K 38/177; A61P 9/10; C07K 14/70596; C07K 2319/30; G01N 33/92; G01N 2333/70596; G01N 2800/323
See application file for complete search history.

(56) References Cited

U.S. PATENT DOCUMENTS

2011/0064746 A1* 3/2011 Liu ............... A61K 38/177 424/172.1
2013/0136739 A1* 5/2013 Zheng ............ A61K 38/177 424/134.1

OTHER PUBLICATIONS

Burgess, et al., Journal of Cell Biology, vol. 111, pp. 2129-2138 (Year: 1990).*
Lazar, et al., Molecular and Cellular Biology, vol. 8, pp. 1247-1252 (Year: 1988).*
Veseli et al., European J Pharmacology 816: 3-13 (Year: 2017).*
Ghetie, V and E.S. Ward, "Multiple Roles for the Major Histocompatibility Complex Class I-Related Receptor FcRn," Annu. Rev. Immunol. vol. 18, pp. 736-766 (2000).
Roopenian, D.C. and S. Akilesh, "FcRn: the Neonatal Fc Receptor Comes of Age," Nature Reviews Immunology, vol. 7, pp. 715-725 (2007).
Roopenian, D.C. et al., "The MHC Class I-Like IgG Receptor Controls Perinatal IgG Transport, IgG Homeostasis, and Fate of IgG-Fc-Coupled Drugs," Jo. Immunol., vol. 170, pp. 3528-3533 (2003).
Ishibashi, S. et al., "Hypercholesterolemia in Low Density Lipoprotein Receptor Knockout Mice and its Reversal by Adenovirus-Mediated Gene Delivery," J. Clin. Invest., vol. 92, pp. 883-893 (1993).
Linton, M.F. et al., "The Role of Lipids and Lipoproteins in Atherosclerosis," Endotext—NCBI Bookshelf, L.J. De Groot et al. (eds.), MDText.com, Inc., South Dartmouth, Mass., pp. 1-96 (2015).
Ridker, P.M. et al., "Cardiovascular Efficacy and Safety of Bococizumab in High-Risk Patients," NEJM, vol. 376, pp. 1527-1539 (2017).
"FDA Approves New Cholesterol Drug," American Heart Association News, pp. 1-2 (Jul. 24, 2015) (newsarchive.heart.org/fda-approves-new-cholesterol-drug, last accessed Nov. 6, 2018).

* cited by examiner

*Primary Examiner* — Phuong Huynh
(74) *Attorney, Agent, or Firm* — Polsinelli PC; Ron Galant

(57) ABSTRACT

The present invention relates to the use of a CD24 protein for lowering low-density lipoprotein cholesterol levels, treating and preventing atherosclerosis, and for reducing risk of cardiovascular disease.

21 Claims, 8 Drawing Sheets
Specification includes a Sequence Listing.

FIG. 1A

MGRAMVARLGLGLLLLALLLPTQIYS**SETTTGTSSNSSQSTSNSGLAP
NPTNATTK**PKSCDKTHTCPPCPAPELLGGPSVFLFPPKPKDTLMISRT
PEVTCVVVDVSHEDPEVKFNWYVDGVEVHNAKTKPREEQYNSTYRVVS
VLTVLHQDWLNGKEYKCKVSNKALPAPIEKTISKAKGQPREPQVYTLP
PSRDELTKNQVSLTCLVKGFYPSDIAVEWESNGQPENNYKTTPPVLDS
DGSFFLYSKLTVDKSRWQQGNVFSCSVMHEALHNHYTQKSLSLSPGK

FIG. 1B

MGRAMVARLGLGLLLLALLLPTQIYS**SETTTGTSSNSSQSTSNSGLAP
NPTNATTKV**PKSCDKTHTCPPCPAPELLGGPSVFLFPPKPKDTLMISR
TPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTL
PPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

FIG. 1C

MGRAMVARLGLGLLLLALLLPTQIYS**SETTTGTSSNSSQSTSNSGLAP
NPTNATTKA**PKSCDKTHTCPPCPAPELLGGPSVFLFPPKPKDTLMISR
TPEVTCVVVDVSHEDPEVKFNWYVDGVEVHNAKTKPREEQYNSTYRVV
SVLTVLHQDWLNGKEYKCKVSNKALPAPIEKTISKAKGQPREPQVYTL
PPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK

FIG. 3

```
Mouse CD24  NQTSVAPFPGN--QNISAS----PNPTNATTRG
            _*  _       *  *  * *      ********__
Human CD24  SETTTGTSS-NSSQSTSNS-GLAPNPTNATTKA(V)
```

FIG. 4a.
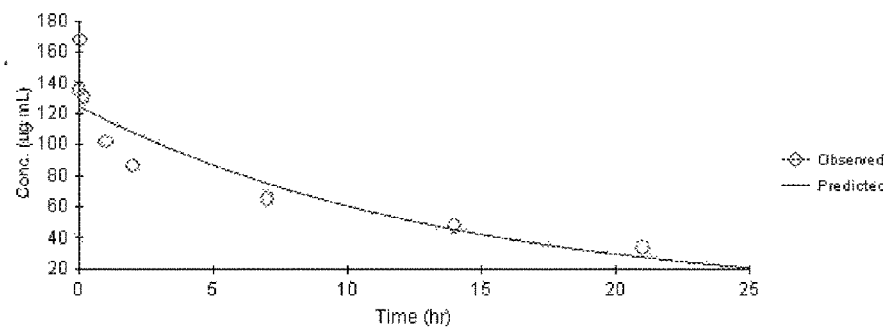
FIG. 4b.
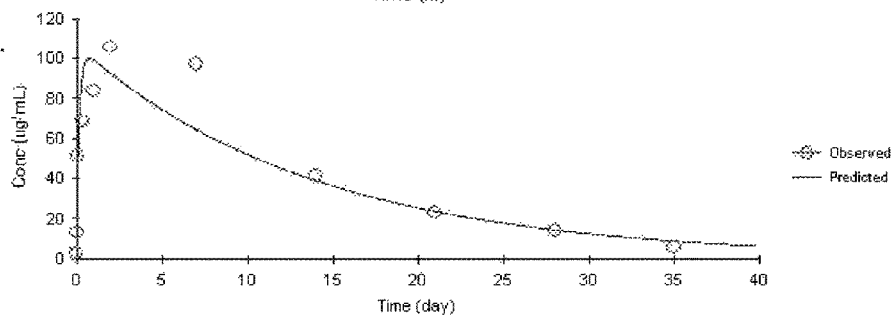
FIG. 4c.
| Routes | Parameter | Units | Estimate | StdError | CV% |
|---|---|---|---|---|---|
| i.v. | AUC | day*ug/mL | 1709.5 | 305.2 | 17.85 |
| s.c | | | 1453.2 | 181.4 | 12.49 |
| i.v. | K10_HL | day | 9.52 | 1.96 | 20.56 |
| s.c | | | 9.54 | 1.43 | 14.97 |
| i.v. | Cmax | ug/mL | 124.4 | 10.3 | 8.31 |
| s.c. | | | 99.6 | 11.1 | 11.11 |

…

USE OF CD24 FOR LOWERING LOW-DENSITY LIPOPROTEIN CHOLESTEROL LEVELS

CROSS-REFERENCE TO RELATED APPLICATIONS

This application is the national stage of International Application No. PCT/US2016/031109 filed May 6, 2016, which claims the benefit of U.S. Provisional Patent Application No. 62/158,157 filed May 7, 2015.

FIELD OF THE INVENTION

The present invention relates to the use of a CD24 protein for lowering low-density lipoprotein cholesterol levels.

REFERENCE TO THE SEQUENCE LISTING

Applicant hereby makes reference to the sequence listing that is contained in the file named "060275-0500-01USPC-Sequence-Listing.txt" (19 KB; created on Nov. 2, 2017), the contents of which are hereby incorporated herein by reference.

BACKGROUND OF THE INVENTION

Dyslipidemia, including high levels of low-density lipoprotein (LDL) cholesterol (LDL-C), is a major risk factor for atherosclerotic cardiovascular disease (ASCVD), which is the leading cause of death and major health care costs worldwide. The association between LDL-C and the risk of ASCVD has been established over decades of genetic and biochemical studies, observational epidemiological and ecological studies, and in vitro and animal experiments. Lowering LDL-C reduces ASCVD events, demonstrating that LDL-C has a central, causal role in coronary heart disease (CHD) and ASCVD. Accordingly, fixed doses of cholesterol-lowering drugs are used as the primary approach for reducing ASCVD risk. In particular, elevated LDL-C is most frequently treated with statins (3-hydroxy-3-methylglutaryl-co-enzyme-A reductase inhibitors). Statins lower LDL-C up to 50% from baseline, and reduce ASCVD risk by 15-37%.

Yet, a residual 60-80% of ASCVD risk remains, which causes major vascular events in about 20% of patients with CHD, even under optimal statin treatment. Moreover, statins can cause muscle symptoms such as pain, tenderness, stiffness, cramping, weakness, fatigue, myopathy, and rhabdomyolysis. Further, although non-statin agents including bile acid-binding resins, fibrates, niacin, and ezetimibe significantly improve lipid profiles, none provides an additional risk reduction for cardiovascular events when combined with a statin. Accordingly, there is a need for improved non-statin drugs for lowering LDL-C levels and reducing the risk of ASCVD.

SUMMARY OF THE INVENTION

Provided herein is a method for reducing LDL-C levels in a subject by administering a CD24 protein to a subject in need thereof. Also provided is a method for treating or preventing atherosclerosis in a subject by administering the CD24 protein to a subject in need thereof. Further provided is a method for lowering the risk of cardiovascular disease, which may be atherosclerotic cardiovascular disease, by administering the CD24 protein to a subject in need thereof. The subject may have an elevated LDL-C, which may be greater than or equal to 70, 75, or 190 mg/dL. The subject may have been previously treated with another LDL-C-lowering drug, which may be a statin or an antagonist of PCSK9.

The CD24 protein may comprise the sequence of a mature human CD24 or a variant thereof. The mature human CD24 may comprise the sequence of SEQ ID NO: 1 or 2. The CD24 protein may comprise any or all of the extracellular domain of human CD24. The CD24 protein may comprise a signal sequence, which may allow secretion from a cell expressing the protein. The signal peptide sequence may comprise the signal peptide of human CD24, which may have SEQ ID NO: 4, or may be one that is found on other transmembrane or secreted proteins, or one modified from the existing signal peptides known in the art. The CD24 protein may be soluble and may be glycosylated. The CD24 protein may be produced using a eukaryotic protein expression system, which may comprise a vector contained in a Chinese Hamster Ovary cell line or a replication-defective retroviral vector. The replication defective retroviral vector may be stably integrated into the genome of a eukaryotic cell.

The CD24 protein may comprise a protein tag, which may be fused at the N- or C-terminus of the CD24 protein. The CD24 protein may comprise a portion of a mammalian immunoglobulin (Ig) protein, which may be human. The portion of the Ig protein may be a Fc region. The Fc region may comprise the hinge region and CH2 and CH3 domains of the Ig protein and the Ig protein may be IgG1, IgG2, IgG3, IgG4, or IgA. The Fc region may also comprise the hinge region and CH2, CH3, and CH4 domains of IgM. The CD24 protein may comprise the sequence of SEQ ID NO: 5, 6, 8, 9, 11, or 12.

Also provided herein is a method of monitoring the activity of the CD24 protein in a subject. The method may comprise comparing the amount of LDL-C in a blood sample obtained from the subject at a time point after administering the CD24 protein to the subject to an amount of LDL-C in a blood sample obtained from the subject before the time point. A decrease in the amount of LDL-C over time may be indicative of an increase in CD24 protein activity. The method may further comprise measuring the amount of LDL-C in the blood sample obtained after administering the CD24 protein to the subject. The method may also comprise measuring the amount of LDL-C in the blood sample obtained from the subject before the time point. The amount of the CD24 protein subsequently administered to the subject may be adjusted according to the amount of LDL-C in the sample obtained after administering the CD24 protein to the subject. The amount of the CD24 protein in the subsequent administration may be adjusted to maintain a specific activity of concentration level of the CD24 protein in the subject.

BRIEF DESCRIPTION OF THE DRAWINGS

FIG. 1A shows the amino acid composition of the full length CD24 fusion protein, CD24Fc (also referred to herein as CD24Ig) (SEQ ID NO: 5). The underlined 26 amino acids are the signal peptide of CD24 (SEQ ID NO: 4), which are cleaved off during secretion from a cell expressing the protein and thus missing from the processed version of the protein (SEQ ID NO: 6). The bold portion of the sequence is the extracellular domain of the mature CD24 protein used in the fusion protein (SEQ ID NO: 2). The last amino acid (A or V) that is ordinarily present in the mature CD24 protein has been deleted from the construct to avoid immunogenicity. The non-underlined, non-bold letters are the sequence of IgG1 Fc, including the hinge region and CH2 and CH3 domains (SEQ ID NO: 7). FIG. 1B shows the sequence of CD24$^V$Fc (SEQ ID NO: 8), in which the mature human CD24 protein (bold) is the valine polymorphic variant of SEQ ID NO: 1. FIG. 1C shows the sequence of CD24$^A$Fc (SEQ ID NO: 9), in which the mature human CD24 protein (bold) is the alanine polymorphic variant of SEQ ID NO: 1. The various parts of the fusion protein in FIGS. 1B and 1C are marked as in FIG. 1A and the variant valine/alanine amino acid is double underlined.

FIG. 3 shows amino acid sequence variations between mature CD24 proteins from mouse (SEQ ID NO: 3) and human (SEQ ID NO: 1). The potential O-glycosylation sites are bolded, and the N-glycosylation sites are underlined.

FIG. 4A-C show WinNonlin compartmental modeling analysis of pharmacokinetics of CD24Fc (CD24Ig) in mice. The opened circles represent the average of 3 mice, and the line is the predicted pharmacokinetic curve. FIG. 4A. i.v. injection of 1 mg CD24Fc. FIG. 4B. s.c. injection of 1 mg CD24Fc. FIG. 4C. Comparison of the total amounts of antibody in the blood as measured by areas under curve (AUC), half-life and maximal blood concentration. Note that overall, the AUC and Cmax of the s.c. injection is about 80% of i.v. injection, although the difference is not statistically significant.

DETAILED DESCRIPTION

Figure 2:
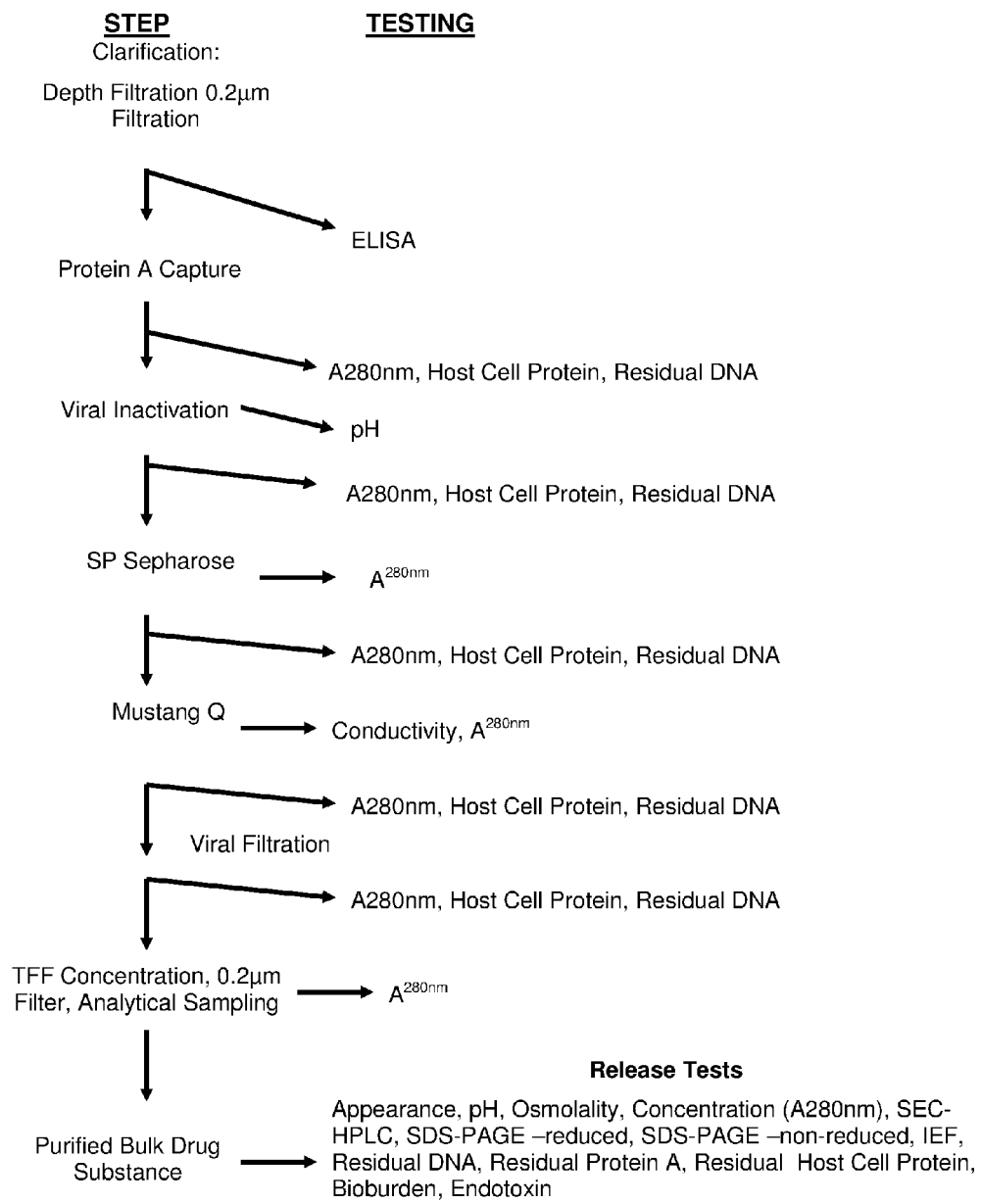
FIG. 2 shows a method for purifying and processing a CD24 protein expressed from mammalian cell lines.

The inventors have found that, surprisingly, proteins containing a mature CD24 sequence are effective for lowering LDL-C levels, and are additionally useful for treating and/or preventing atherosclerosis, and for reducing the risk of cardiovascular disease such as atherosclerotic cardiovascular disease. As described in more detail herein, CD24 is a small glycosyl-phosphatidyl-inositol (GPI)-anchored glycoprotein with widespread expression among both hematopoietic and non-hematopoietic cells, which is encoded by a coding sequence of 240 base pairs. Of the 80 amino acids, the first 26 constitute the signal peptide, while the last 23 serve as a signal for cleavage to allow for the attachment of the GPI tail. As a result, the mature human CD24 molecule has only 31 amino acids. Amino acid 31 is polymorphic among the human population. A C to T transition at nucleotide 226 results in the substitution of alanine (A) with valine (V). Since this residue is in the position immediately N-terminal to the cleavage site, and since the replacement is non-conservative, these two alleles may be expressed at different efficiencies on the cell surface. Transfection studies with copy DNA demonstrated that CD24$^{v/v}$ alleles are more efficiently expressed on the cell surface. Consistent with this, CD24$^{v/v}$ peripheral blood leukocytes expressed higher levels of CD24, especially on T cells. Three lines of evidence demonstrate that CD24 is a genetic modifier for MS. At the population level, the CD24$^{v/v}$ genotype is more than twice as frequent as it is in the normal population. Among multiplex MS families, the CD24$^v$ allele is preferentially transmitted to the MS patients in comparison to healthy controls. Furthermore, among the MS patients who have a more severe form of the disease (Expanded Disability Status Scale [EDSS] at or exceeding 6.0, when the patients lose the ability to walk independently), CD24$^{v/v}$ individuals took, on average, 7 years to reach EDSS 6.0 from the first clinical symptom, yet the CD24$^{a/v}$ or CD24$^{a/a}$ individuals reached EDSS 6.0 in 13 to 15 years. Conversely, a dinucleotide deletion in the 3' untranslated region of CD24 messenger ribonucleic acid (mRNA), which reduces CD24 mRNA stability and thus reduces CD24 expression, protects humans against MS and other autoimmune diseases. To date, CD24 has not been shown to affect lipid levels.

1. Definitions

The terminology used herein is for the purpose of describing particular embodiments only and is not intended to be limiting. As used in the specification and the appended claims, the singular forms "a," "an" and "the" include plural referents unless the context clearly dictates otherwise.

For recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the numbers 6.0, 6.1, 6.2, 6.3, 6.4, 6.5, 6.6, 6.7, 6.8, 6.9, and 7.0 are explicitly contemplated.

A "peptide" or "polypeptide" is a linked sequence of amino acids and may be natural, synthetic, or a modification or combination of natural and synthetic.

"Substantially identical" may mean that a first and second amino acid sequence are at least 60%, 65%, 70%, 75%, 80%, 85%, 90%, 95%, 96%, 97%, 98%, or 99% over a region of 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 55, 60, 65, 70, 75, 80, 85, 90, 95, 100, 110, 120, 130, 140, 150, 160, 170, 180, 190, 200, 210, 220, 230, 240, 250, 260, 270, 280, 290, or 300 amino acids.

"Treatment" or "treating," when referring to protection of an animal from a disease, means preventing, suppressing, repressing, or completely eliminating the disease. Preventing the disease involves administering a composition of the present invention to an animal prior to onset of the disease. Suppressing the disease involves administering a composition of the present invention to an animal after induction of the disease but before its clinical appearance. Repressing the disease involves administering a composition of the present invention to an animal after clinical appearance of the disease.

A "variant" may mean a peptide or polypeptide that differs in amino acid sequence by the insertion, deletion, or conservative substitution of amino acids, but retain at least one biological activity. Representative examples of "biological activity" include the ability to bind to a toll-like receptor and to be bound by a specific antibody. Variant may also mean a protein with an amino acid sequence that is substantially identical to a referenced protein with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change. These minor changes can be identified, in part, by considering the hydropathic index of amino acids, as understood in the art. Kyte et al., J. Mol. Biol. 157:105-132 (1982). The hydropathic index of an amino acid is based on a consideration of its hydrophobicity and charge. It is known in the art that amino acids of similar hydropathic indexes can be substituted and still retain protein function. In one aspect, amino acids having hydropathic indexes of ±2 are substituted. The hydrophilicity of amino acids can also be used to reveal substitutions that would result in proteins retaining biological function. A consideration of the hydrophilicity of amino acids in the context of a peptide permits calculation of the greatest local average hydrophilicity of that peptide, a useful measure that has been reported to correlate well with antigenicity and immunogenicity. U.S. Pat. No. 4,554,101, incorporated fully herein by reference. Substitution of amino acids having similar hydrophilicity values can result in peptides retaining biological activity, for example immunogenicity, as is understood in the art. Substitutions may be performed with amino acids having hydrophilicity values within ±2 of each other. Both the hyrophobicity index and the hydrophilicity value of amino acids are influenced by the particular side chain of that amino acid. Consistent with that observation, amino acid substitutions that are compatible with biological function are understood to depend on the relative similarity of the amino acids, and particularly the side chains of those amino acids, as revealed by the hydrophobicity, hydrophilicity, charge, size, and other properties.

2. CD24

Provided herein is a CD24 protein, which may comprise the amino acid sequence of mature human CD24 or those from other mammals, which corresponds to the extracellular domain (ECD) of CD24, or a variant thereof. As described above, the sequence of the mature human CD24 protein is 31 amino acids long with a variable alanine (A) with valine (V) residue at its C-terminal end:

SETTTGTSSNSSQSTSNSGLAPNPTNATTK(V/A) (SEQ ID NO: 1)

The C-terminal valine or alanine may be immunogenic and may be omitted from the CD24 protein to reduce its immunogenicity. Therefore, the CD24 protein may comprise the amino acid sequence or mature human CD24 lacking the C-terminal amino acid:

SETTTGTSSNSSQSTSNSGLAPNPTNATTK (SEQ ID NO: 2)

Despite considerable sequence variations in the amino acid sequence of the mature CD24 proteins from mouse and human, they are functionally equivalent, as human CD24Fc has been shown to be active in the mouse. The amino acid sequence of the human CD24 ECD shows some sequence conservation with the mouse protein (39% identity; GenBank accession number NP_033976), as shown in FIG. 3. However, it is not that surprising that the percent identity is not higher as the CD24 ECD is only 27-31 amino acids in length, depending on the species, and binding to some of its receptor(s), such as Siglec 10/G, is mediated by its sialic acid and/or galactose sugars of the glycoprotein. The amino acid sequence identity between the extracellular domains of the human Siglec-10 (GenBank accession number AF310233) and its murine homolog Siglec-G (GenBank accession number NP_766488) receptor proteins is 63%. As a result of sequence conservation between mouse and human CD24 primarily in the C-terminus and in the abundance of glycosylation sites, significant variations in the mature CD24 proteins may be tolerated in using the CD24 protein, especially if those variations do not affect the conserved residues in the C-terminus or do not affect the glycosylation sites from either mouse or human CD24. Therefore, the CD24 protein may comprise the amino acid sequence of mature murine CD24:

NQTSVAPFPGNQNISASPNPTNATTRG (SEQ ID NO: 3).

The amino acid sequence of the human CD24 ECD shows more sequence conservation with the cynomolgus monkey protein (52% identity; UniProt accession number UniProtKB-I7GKK1) than with mouse. Again, this is not surprising given that the percent identity is not higher as the ECD is only 29-31 amino acids in length in these species, and the role of sugar residues in binding to its receptor(s). The amino acid sequence of cynomolgous Siglec-10 receptor has not been determined but the amino acid sequence identity between the human and rhesus monkey Siglec-10 (GenBank accession number XP_001116352) proteins is 89%. Therefore, the CD24 protein may also comprise the amino acid sequence of mature cynomolgous (or rhesus) monkey CD24:

TVTTSAPLSSNSPQNTSTTPNPANTTTKA (SEQ ID NO: 10)

The CD24 protein may be soluble. The CD24 protein may comprise an N-terminal signal peptide, to allow secretion from a cell expressing the protein. The signal peptide sequence may comprise the amino acid sequence MGRAMVARLGLGLLLLALLLPTQIYS (SEQ ID NO: 4). Alternatively, the signal sequence may be any of those that are found on other transmembrane or secreted proteins, or those modified from the existing signal peptides known in the art.

a. Fusion

The CD24 protein may be fused at its N- or C-terminal end to a protein tag. The protein tag may comprise a portion of a mammalian Ig protein, which may be human or mouse or another species. The portion may comprise an Fc region of the Ig protein. The Fc region may comprise at least one of the hinge region, CH2, CH3, and CH4 domains of the Ig protein. The Ig protein may be human IgG1, IgG2, IgG3, IgG4, or IgA, and the Fc region may comprise the hinge region, and CH2 and CH3 domains of the Ig. The Fc region may comprise the human immunoglobulin G1 (IgG1) isotype, which may have the sequence of SEQ ID NO: 7. The Ig protein may also be IgM, and the Fc region may comprise the hinge region and CH2, CH3, and CH4 domains of IgM. The protein tag may be an affinity tag that aids in the purification of the protein, or a solubility-enhancing tag that enhances the solubility and recovery of functional proteins. The protein tag may also increase the valency of the CD24 protein. The protein tag may also comprise GST, His, FLAG, Myc, MBP, NusA, thioredoxin (TRX), small ubiquitin-like modifier (SUMO), ubiquitin (Ub), albumin, or a Camelid Ig. Methods for making fusion proteins and purifying fusion proteins are well known in the art.

Based on preclinical research, for the construction of the fusion protein CD24Fc identified in the examples, the truncated form of native CD24 molecule of 30 amino acids, which lacks the final polymorphic amino acid before the GPI signal cleavage site (that is, a mature CD24 protein having SEQ ID NO: 2), has been used. The mature human CD24 sequence is fused to a human IgG1 Fc domain (SEQ ID NO: 7). The full length CD24Fc fusion protein is provided in SEQ ID NO: 5 (FIG. 1), and the processed version of CD24Fc fusion protein that is secreted from the cell (i.e. lacking the signal sequence which is cleaved off) is provided in SEQ ID NO: 6. Processed polymorphic variants of mature CD24 (that is, mature CD24 protein having SEQ ID NO: 1) fused to IgG1 Fc may comprise SEQ ID NO: 11 or 12.

b. Production

The CD24 protein may be heavily glycosylated, and may be involved in functions of CD24 such as costimulation of immune cells and interaction with a damage-associated molecular pattern molecule (DAMP). The CD24 protein may be prepared using a eukaryotic expression system. The expression system may entail expression from a vector in mammalian cells, such as Chinese Hamster Ovary (CHO) cells. The system may also be a viral vector, such as a replication-defective retroviral vector that may be used to infect eukaryotic cells. The CD24 protein may also be produced from a stable cell line that expresses the CD24 protein from a vector or a portion of a vector that has been integrated into the cellular genome. The stable cell line may express the CD24 protein from an integrated replication-defective retroviral vector. The expression system may be GPEx™.

c. Pharmaceutical Composition

The CD24 protein may be contained in a pharmaceutical composition, which may comprise a pharmaceutically acceptable amount of the CD24 protein. The pharmaceutical composition may comprise a pharmaceutically acceptable carrier. The pharmaceutical composition may comprise a solvent, which may keep the CD24 protein stable over an extended period. The solvent may be PBS, which may keep the CD24 protein stable for at least 66 months at −20° C. (−15~−25° C.). The solvent may be capable of accommodating the CD24 protein in combination with another drug.

The pharmaceutical composition may be formulated for parenteral administration including, but not limited to, by injection or continuous infusion. Formulations for injection may be in the form of suspensions, solutions, or emulsions in oily or aqueous vehicles, and may contain formulation agents including, but not limited to, suspending, stabilizing, and dispersing agents. The composition may also be provided in a powder form for reconstitution with a suitable vehicle including, but not limited to, sterile, pyrogen-free water.

The pharmaceutical composition may also be formulated as a depot preparation, which may be administered by implantation or by intramuscular injection. The composition may be formulated with suitable polymeric or hydrophobic materials (as an emulsion in an acceptable oil, for example), ion exchange resins, or as sparingly soluble derivatives (as a sparingly soluble salt, for example).

d. Dosage

The dose of the CD24 protein may ultimately be determined through a clinical trial to determine a dose with acceptable toxicity and clinical efficacy. The initial clinical dose may be estimated through pharmacokinetics and toxicity studies in rodents and non-human primates. The dose of the CD24 protein may be 0.01 mg/kg to 1000 mg/kg, and may be 1 to 500 mg/kg, depending on the desired amount of LDL-C-lowering and the route of administration. The CD24 protein may be administered by intravenous infusion or subcutaneous or intramural (that is, within the wall of a cavity or organ) injection, and the dose may be 10-1000 mg, 10-500 mg, 10-240 mg, 10-120 mg, or 10, 30, 60, 120, or 240 mg, where the subject is a human.

3. Methods of Treatment

The CD24 protein may be administered to a subject to lower LDL-C levels, which may be elevated, and may further be elevated above a normal range. The normal range may be defined by a standard known in the art, such as National Cholesterol Education Panel Adult Treatment Panel (ATP) III or the 2005 update thereto (described in Circulation 2002; 106:3143-421; and J Am Coll Cardiol. 2004 Aug. 4; 44(3):720-32; the contents of both which are incorporated herein by reference), or as set forth by the National Institute for Health and Care Excellence (NICE). The subject may have a lysosomal acid lipase (LAL) deficiency, familial hypercholesterolemia, or hyperlipidemia. The CD24 protein may also be administered to a subject to treat or prevent atherosclerosis, or to lower the risk of a cardiovascular disease event, which may be an atherosclerotic cardiovascular disease (ASCVD) event. The ASCVD event may be an acute coronary syndrome, myocardial infarction, stable or unstable angina, a coronary or other arterial revascularization, stroke, transient ischemic attack, or peripheral arterial disease presumed to be of atherosclerotic origin. The subject may be a mammal such as a human.

The subject may be a male or female. The subject may be of any age, but in particular may have an age of 40-75 years, or greater than 75 years. The subject may have a LDL-C greater than or equal to 70 mg/dL, 75 mg/dL, or 190 mg/dL. The subject may also be diabetic or non-diabetic, be 40-75 years old, and have a LDL-C of 70-189 mg/dL. The subject may have a 10-year ASCVD risk (defined as nonfatal myocardial infarction, coronary heart disease death, or nonfatal and fatal stroke) greater than or equal to 7.5%, or of 5-7.5%. The subject may have characteristics of a subject for whom LDL-C lowering is recommended according to the 2013 American College of Cardiology/American Heart Association Guidelines (Stone N J, et al., 2013 ACC/AHA guideline of the treatment of blood cholesterol to reduce atherosclerotic cardiovascular risk in adults: a report of the American College of Cardiology/American Heart Association Task Force on Practice Guidelines, J Am Coll Cardiol 2014; 63:2889-934). The subject may have familial hypercholesterolemia, which may be caused by a mutation in the LDL receptor gene, apolipoprotein B gene, or pro-protein convertase subtilisin/kexintype 9 gene.

The subject may have been previously treated with a LDL-C-lowering drug, such as a statin. The subject may also have experienced an adverse event as a result of the drug. The adverse event may have been a muscle symptom such as pain, tenderness, stiffness, cramping, weakness, or general fatigue, and may have been a creatine phosphokinase level indicative of an increased risk for adverse muscle events (which may be >10 times the upper limit of normal). The subject may be recalcitrant to treatment with another cholesterol-lowering drug, and may have a LDL-C greater than or equal to 75 mg/dL after being treated with the other drug, which may be a statin. The subject may have graft vs. host disease, and may have exhibited a 10% or greater increase in LDL-C after having undergone a transplant in comparison to the subject's LDL-C before the transplant. The subject may have multiple sclerosis, rheumatoid arthritis, or an autoimmune or inflammatory disease.

a. Administration

The route of administration of the pharmaceutical composition may be parenteral. Parenteral administration includes, but is not limited to, intravenous, intraarterial, intraperitoneal, subcutaneous, intramuscular, intrathecal, intraarticular, and direct injection. The pharmaceutical composition may be administered to a human patient, cat, dog, large animal, or an avian. The composition may be administered 1, 2, 3, 4, 5, 6, 7, 8, 9, 10, 11, or 12 times per day.

b. Combination Treatment

The CD24 protein may be combined with another treatment such as a drug, including a statin, a bile acid-binding resin, fibrate, niacin, ezetimibe, or a drug that increases LDL receptor levels, including but not limited to an antibody or other inhibitor that antagonizes or blocks the function of PCSK9. The CD24 protein and the other drug may be administered together or sequentially.

The CD24 protein may be administered simultaneously or metronomically with other treatments. The term "simultaneous" or "simultaneously" as used herein, means that the CD24 protein and other treatment be administered within 48 hours, preferably 24 hours, more preferably 12 hours, yet more preferably 6 hours, and most preferably 3 hours or less, of each other. The term "metronomically" as used herein means the administration of the agent at times different from the other treatment and at a certain frequency relative to repeat administration.

The CD24 protein may be administered at any point prior to another treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins, 10 mins, 9 mins, 8 mins, 7 mins., 6 mins., 5 mins., 4 mins., 3 mins, 2 mins, and 1 mins. The CD24 protein may be administered at any point prior to a second treatment of the CD24 protein including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., 30 mins., 25 mins., 20 mins., 15 mins., 10 mins., 9 mins., 8 mins., 7 mins., 6 mins., 5 mins., 4 mins., 3 mins, 2 mins, and 1 mins.

The CD24 protein may be administered at any point after another treatment including about 1 min, 2 mins., 3 mins., 4 mins., 5 mins., 6 mins., 7 mins., 8 mins., 9 mins., 10 mins., 15 mins., 20 mins., 25 mins., 30 mins., 35 mins., 40 mins., 45 mins., 50 mins., 55 mins., 1 hr, 2 hr, 3 hr, 4 hr, 6 hr, 8 hr, 10 hr, 12 hr, 14 hr, 16 hr, 18 hr, 20 hr, 22 hr, 24 hr, 26 hr, 28 hr, 30 hr, 32 hr, 34 hr, 36 hr, 38 hr, 40 hr, 42 hr, 44 hr, 46 hr, 48 hr, 50 hr, 52 hr, 54 hr, 56 hr, 58 hr, 60 hr, 62 hr, 64 hr, 66 hr, 68 hr, 70 hr, 72 hr, 74 hr, 76 hr, 78 hr, 80 hr, 82 hr, 84 hr, 86 hr, 88 hr, 90 hr, 92 hr, 94 hr, 96 hr, 98 hr, 100 hr, 102 hr, 104 hr, 106 hr, 108 hr, 110 hr, 112 hr, 114 hr, 116 hr, 118 hr, and 120 hr. The CD24 protein may be administered at any point prior after a previous CD24 treatment including about 120 hr, 118 hr, 116 hr, 114 hr, 112 hr, 110 hr, 108 hr, 106 hr, 104 hr, 102 hr, 100 hr, 98 hr, 96 hr, 94 hr, 92 hr, 90 hr, 88 hr, 86 hr, 84 hr, 82 hr, 80 hr, 78 hr, 76 hr, 74 hr, 72 hr, 70 hr, 68 hr, 66 hr, 64 hr, 62 hr, 60 hr, 58 hr, 56 hr, 54 hr, 52 hr, 50 hr, 48 hr, 46 hr, 44 hr, 42 hr, 40 hr, 38 hr, 36 hr, 34 hr, 32 hr, 30 hr, 28 hr, 26 hr, 24 hr, 22 hr, 20 hr, 18 hr, 16 hr, 14 hr, 12 hr, 10 hr, 8 hr, 6 hr, 4 hr, 3 hr, 2 hr, 1 hr, 55 mins., 50 mins., 45 mins., 40 mins., 35 mins., mins., 25 mins., 20 mins., 15 mins., 10 mins., 9 mins., 8 mins., 7 mins., 6 mins., 5 mins., 4 mins., 3 mins, 2 mins, and 1 mins.

4. Methods of Monitoring CD24 Protein Activity

The activity of the CD24 protein administered to a subject may be monitored by detecting the concentration of LDL-C in the subject. The subject may be undergoing treatment with the CD24 protein, such as treatment for multiple sclerosis, rheumatoid arthritis, graft-versus-host disease, immune-mediated tissue injury, and the like. The concentration of LDL-C may be indicative of the level of CD24 protein activity in the subject, where a decrease in LDL-C in the patient indicates greater CD24 protein activity. The method may comprise obtaining a sample from the subject and detecting the amount of LDL-C in the sample. The sample may be a blood sample such as serum or plasma. Methods of measuring LDL-C concentrations are well-known in the art, such as an ELISA based assay or a Colorimetric/Fluorometric assay following cholesterol esterase and cholesterol oxidase treatment. The amount of LDL-C may be measured by the Friedewald calculation, which may comprise calculating the amount of LDL-C based on amounts of total cholesterol, triglycerides, and high-density lipoprotein cholesterol (HDL-C) measured in the sample. The amount of HDL-C may be measured either by a precipitation procedure with dextran sulfate-$Mg^{2+}$ or by a direct HDL-C assay. The amount of LDL-C may also be measured by the DIRECT LDL™ assay, the homogeneous N-GENEOUS™ LDL assay, or calculated LDL-C values deriving from the ApoB based equation: 0.41TC-0.32TG+1.70ApoB-0.27, (Clin Chem 1997; 43:808-815; the contents of which are incorporated herein by reference). The level of LDL-C can be monitored over time and during the course of CD24 protein treatment in order to monitor the response to treatment.

The amount of CD24 protein being administered to the subject, for treating an indication described herein or known in the art, may be adjusted based on the level of CD24 protein activity detected using LDL-C. The level of LDL-C can be monitored over a period of time or during the course of CD24 protein treatment. If the LDL-C concentration in the subject is reduced to a level within the range of normal, then the amount of CD24 protein administered to the subject may be reduced, such as by lowering the dose of CD24 protein or administering it less frequently. If the LDL-C concentration remains unchanged or remains above the range of normal, then the amount of CD24 protein administered to the subject may be increased, such as by increasing the dose of CD24 protein or administering it more frequently. As an alternative to LDL-C, the concentration of LDL particles (LDL-P) may also be measured to monitor CD24 protein activity. The LDL-P concentration may be detected directly using NMR.

Levels of the CD24 protein administered to the subject may also be monitored, which may be by a method comprising obtaining a sample from the subject and detecting the amount of the CD24 protein in the sample. The sample may be a blood sample such serum or plasma. Protein detection methods are well-known in the art. The CD24 protein in the sample may be detected by any protein detection method, such as an immunoassay including ELISA, Gyros, MSD, Biacore, AlphaLISA, Delfia, Singulex, Luminex, Immuno-PCR, Cell-based assays, RIA, Western blot, an affinity column, and the like. The ELISA method may be sandwich ELISA or competitive ELISA. For example, the ELISA may comprise contacting the sample to an anti-CD24 protein antibody, contacting the CD24 protein-CD24 protein antibody complex with a labeled antibody that binds to the anti-CD24 protein antibody, and measuring the amount of labeled antibody by detecting a signal produced by the label, where the amount of signal correlates to the amount of CD24 protein in the sample.

The amount of CD24 protein administered to the subject may be adjusted (such as by adjusting dose and frequency of administration) based on a pharmacokinetic parameter for the CD24 protein. For example, the amount of CD24 protein administered to the subject may be adjusted to obtain a plasma CD24 concentration of greater than 1 ng/ml. In another example, the amount of CD24 protein administered to the subject is adjusted to maintain a steady state plasma concentration greater than 1 ng/mL. In another example, the amount of CD24 protein administered to the subject may be adjusted to obtain a $C_{max}$ of the CD24 protein of at least about 1 ng/mL. In yet another example, the amount of CD24 protein administered to the subject may be adjusted to achieve a drug exposure level, as defined by the $AUC_{0-inf}$ of the CD24 protein of at least about 400,000 ng*hr/mL.

The present invention has multiple aspects, illustrated by the following non-limiting examples.

Example 1

Making Soluble CD24 Proteins

The mature sequence of CD24 was fused to IgG1 Fc. The amino acid composition of the CD24 fusion protein is provided in FIG. 1. A replication-defective retroviral vector that drives expression of the CD24Fc fusion protein was then generated. The GPEx™ (an acronym for gene product expression) system offers several important advantages, the most important of which is the, on average, >1000 insertions/cell but with only 1 copy/insertion. Moreover, since the retrovirus preferentially inserts into the transcriptional active locus, the GPEx™ resulted in a high level of expression of the targeted protein. Stable cell lines that produce a high yield of CD24Fc were generated. In addition 45 grams of GLP grade products and ~100 grams of cGMP grade products were produced. The methods used for downstream processing of media harvested from the bioreactor are summarized in the flow chart below (FIG. 2).

Harvest Clarification

The bioreactor culture media was clarified using Cuno 60M02 Maximizer depth filters followed by a Millipore Opticap 0.22 um filter. The filtrate was collected into a sterile collection bag. Samples were obtained for CD24-Fc yield quantitation by ELISA.

Protein A Capture

The clarified media was passed over a column of Protein A resin (GE Healthcare MabSelect) at a concentration not exceeding 16 g/L of resin (based on ELISA) and a contact time of 4 minutes. The column was washed with the equilibration buffer (50 mM Tris+0.15M NaCl pH7.5), then with 10 mM sodium citrate/citric acid pH 6.0 for 5cvs. Bound CD24Fc was eluted from the column using 10 mM sodium citrate/citric acid pH 3.5

Viral Inactivation

The Protein A eluate fraction was immediately brought to pH 3.0 with the addition of 2M Hydrochloric acid and held at this pH for 30 minutes at ambient temperature. It was then brought to pH 5.0 with the addition of 1M Tris base, and filtered to clarity using a 0.65 um glass fiber filter (Sartorius Sartopure GF2) and 0.2 um (Sartorius Sartopore 2) into a sterile collection bag.

SP-Sepharose Chromatography

The viral inactivated material was applied to a column of SP-Sepharose (GE Healthcare) at a concentration not exceeding 25 g/L of resin (based on A280 nm of 1.22=1 mg/mL) and a linear flow rate of 250 cm/hr. The column was washed with the equilibration buffer (10 mM sodium citrate/citric acid pH 5.0) and bound CD24Fc was eluted from the column using 10 mM sodium citrate/citric acid+0.2M NaCl pH5.0. The effluent was collected into a sterile collection bag.

Mustang Q Chromatography

The SP-Sepharose elute was adjusted to pH 7.5 by the addition of 1M Tris base and diluted with WFI to reduce the conductivity. The diluted material was applied to a Mustang Q filter (Pall) at a concentration not exceeding 0.5 g/L of resin (based on A280 nm of 1.22=1 mg/mL) and at a flow rate of 5 column volumes/minute. The filter was washed with the equilibration buffer (10 mM Tris pH 7.5) and the CD24-Fc is contained in the flow through and is collected into a sterile collection bag.

Viral Filtration

The Mustang Q flow through was then filtered at a constant pressure of 30 psi through a 0.2 mM filter and a Millipore NFP viral filter (nominal pore size 20 nm) and was collected into a sterile collection bag.

Concentration and Final Formulation

The product was concentrated and diafiltered using a 10 kDa ultrafiltration membrane (Millipore Prep/Scale) into a 10 mM sodium phosphate, 150 mM sodium chloride pH 7.2 at approximately 10 mg/mL final concentration as determined by absorbance at 280 nm. Analytical samples were drawn from the bulk whilst in a biosafety cabinet. Labeling was performed and the samples were delivered to QC for testing while the bulk aliquots were stored at 2-8° C. pending release.

Example 2

CD24 Pharmacokinetics in Mice 1 mg of CD24Fc (CD24Fc) was injected into naïve C57BL/6 mice and collected blood samples at different timepoints (5 min, 1 hr, 4 hrs, 24 hrs, 48 hrs, 7 days, 14 days and 21 days) with 3 mice in each timepoint. The sera were diluted 1:100 and the levels of CD24Fc was detected using a sandwich ELISA using purified anti-human CD24 (3.3 μg/ml) as the capturing antibody and peroxidase conjugated goat anti-human IgG Fc (5 μg/ml) as the detecting antibodies. As shown in FIG. 4a. The decay curve of CD24Fc revealed a typical biphase decay of the protein. The first biodistribution phase had a half-life of 12.4 hours. The second phase follows a model of first-order elimination from the central compartment. The half-life for the second phase was 9.54 days, which is similar to that of antibodies in vivo. These data suggest that the fusion protein is very stable in the blood stream. In another study in which the fusion protein was injected subcutaneously, an almost identical half-life of 9.52 days was observed (FIG. 4b). More importantly, while it took approximately 48 hours for the CD24Fc to reach peak levels in the blood, the total amount of the fusion protein in the blood, as measured by AUC, was substantially the same by either route of injection. Thus, from therapeutic point of view, different route of injection should not affect the therapeutic effect of the drug. This observation greatly simplified the experimental design for primate toxicity and clinical trials.

Example 3

CD24 Lowers LDL-C Levels

This example demonstrates that CD24 lowers LDL-C. Changes of fasting LDL-C in plasma from baseline were analyzed in a clinical study which is described in more detail below (see the Methods section of this example). Fasting LDL-C levels were determined among samples obtained on Day −1, Day 7, and Day 42 for Cohort 1 (CD24Fc 10 mg group). Beginning with Cohort 2 (CD24Fc 30 mg group), this lipid sampling was expanded to include Day 14. The data are summarized in Table 1. Due to an incomplete dataset in Cohort 1, Cohorts 2-5 were used to analyze for dose-dependent reduction of LDL-C levels. A statistically significant dose-dependent reduction was observed (Table 1).

TABLE 1

Change in LDL-C levels on Day 7 (U1), Day 14 (U2) and Day 42 (U3) from baseline (U0, defined as 100%)

| Dose | Obs | Variable | Label | N | Mean | Std Dev | Minimum | Maximum |
|---|---|---|---|---|---|---|---|---|
| 10 mg | 6 | u0 | Baseline LDL | 6 | 100.0000000 | 0 | 100.0000000 | 100.0000000 |
|  |  | u1 | 7 days LDL ratio | 5 | 99.6785886 | 8.5665505 | 87.0370370 | 107.7586207 |
|  |  | u2 | 14 days LDL ratio | 0 | . | . | . | . |
|  |  | u3 | 42 days LDL ratio | 6 | 102.9957054 | 5.3134796 | 96.8085106 | 110.5769231 |
| 30 mg | 6 | u0 | Baseline LDL | 6 | 100.0000000 | 0 | 100.0000000 | 100.0000000 |
|  |  | u1 | 7 days LDL ratio | 6 | 96.9190313 | 9.5257894 | 86.9047619 | 113.4328358 |
|  |  | u2 | 14 days LDL ratio | 6 | 97.5816504 | 15.2482354 | 84.5238095 | 122.3880597 |
|  |  | u3 | 42 days LDL ratio | 6 | 106.1959745 | 8.2383407 | 95.2830189 | 113.4328358 |
| 60 mg | 6 | u0 | Baseline LDL | 6 | 100.0000000 | 0 | 100.0000000 | 100.0000000 |
|  |  | u1 | 7 days LDL ratio | 6 | 90.7620588 | 12.6697467 | 72.0720721 | 106.1728395 |
|  |  | u2 | 14 days LDL ratio | 6 | 102.5671170 | 5.2461286 | 96.5517241 | 110.3773585 |
|  |  | u3 | 42 days LDL ratio | 6 | 105.1546943 | 13.4340830 | 93.2773109 | 127.1604938 |
| 120 mg | 6 | u0 | Baseline LDL | 6 | 100.0000000 | 0 | 100.0000000 | 100.0000000 |
|  |  | u1 | 7 days LDL ratio | 6 | 87.1476632 | 16.0595374 | 61.7391304 | 106.4516129 |
|  |  | u2 | 14 days LDL ratio | 6 | 95.2625418 | 11.8341667 | 83.4782609 | 116.1290323 |
|  |  | u3 | 42 days LDL ratio | 6 | 100.1377165 | 9.9404474 | 87.1794872 | 112.3456790 |
| 240 mg | 6 | u0 | Baseline LDL | 6 | 100.0000000 | 0 | 100.0000000 | 100.0000000 |
|  |  | u1* | 7 days LDL ratio | 6 | 84.6472221 | 7.6553896 | 71.5596330 | 94.0476190 |
|  |  | u2* | 14 days LDL ratio | 5 | 90.1393086 | 5.2501807 | 86.2385321 | 99.0825688 |
|  |  | u3 | 42 days LDL ratio | 6 | 107.0369419 | 14.7154796 | 79.8449612 | 121.1009174 |

TABLE 1-continued

Change in LDL-C levels on Day 7 (U1), Day 14 (U2) and Day 42 (U3) from baseline (U0, defined as 100%)

| Dose | Obs | Variable | Label | N | Mean | Std Dev | Minimum | Maximum |
|---|---|---|---|---|---|---|---|---|
| Control | 10 | u0 | Baseline LDL | 10 | 100.0000000 | 0 | 100.0000000 | 100.0000000 |
| | | u1 | 7 days LDL ratio | 10 | 93.7350811 | 8.9747121 | 83.7837838 | 107.1428571 |
| | | u2 | 14 days LDL ratio | 8 | 104.5965396 | 13.8625952 | 83.7837838 | 125.2631579 |
| | | u3 | 42 days LDL ratio | 10 | 102.6699920 | 16.2815599 | 77.0270270 | 138.1578947 |

*P < 0.05 when compared to placebo group, student t-test.

Using cohort 1 as reference, it was determined whether CD24Fc reduced LDL-C levels in a dose- and time-dependent manner. As shown in Table 2, compared with cohort 1 which received 10 mg of CD24Fc, a significant dose-dependent reduction of LDL-C levels was observed (p<0.0001).

TABLE 2

Dose and time-dependence of LDL-C reduction in Cohorts by GEE model, using cohort 1 (the lowest dose as reference)

| Parameter | Estimate | Standard Error | 95% Confidence Limits | | Z | Pr > |Z| |
|---|---|---|---|---|---|---|
| Intercept | 98.0544 | 5.4745 | 87.3245 | 108.7842 | 17.91 | <.0001 |
| time | 1.6471 | 2.1861 | −2.6375 | 5.9317 | 0.75 | 0.4512 |
| 30 mg | 3.7167 | 7.3244 | −10.6389 | 18.0722 | 0.51 | 0.6118 |
| time * 30 mg | −1.4733 | 3.5435 | −8.4183 | 5.4718 | −0.42 | 0.6776 |
| 60 mg | −25.4898 | 14.4124 | −53.7377 | 2.7581 | −1.77 | 0.0770 |
| time * 60 mg | 10.7245 | 5.0225 | 0.8805 | 20.5685 | 2.14 | 0.0327 |
| 120 mg | −21.2684 | 9.4771 | −39.8431 | −2.6936 | −2.24 | 0.0248 |
| time * 120 mg | 6.6669 | 3.9357 | −1.0468 | 14.3806 | 1.69 | 0.0903 |
| 240 mg | −15.8681 | 6.9247 | −29.4402 | −2.2960 | −2.29 | 0.0219 |
| time * 240 mg | 5.4390 | 2.8825 | −0.2106 | 11.0887 | 1.89 | 0.0592 |

A statistically significant dose-dependent reduction of LDL-C was observed, indicating that CD24Fc is effective for lowering LDL-C in human patients.

Methods

This was a Phase I, randomized, double-blind, placebo-controlled, single ascending dose study to assess the safety, tolerability, and PK of CD24Fc in healthy male and female adult subjects. A total of 40 subjects in 5 cohorts of 8 subjects each were enrolled in this study. Six of the 8 subjects in each cohort received study drug and 2 subjects received placebo (0.9% sodium chloride, saline). The first cohort was dosed with 10 mg. Succeeding cohorts received 30 mg, 60 mg, 120 mg, and 240 mg of CD24Fc or matching placebo and were dosed at least 3 weeks apart to allow for review of safety and tolerability data for each prior cohort. Administration of the next higher dose to a new cohort of subjects was permitted only if adequate safety and tolerability had been demonstrated.

In each cohort, the initial 2 subjects were 1 study drug recipient and 1 placebo recipient on Day 1. The 3rd to 5th and 6th to 8th subjects were dosed after Day 7 (a minimum of 24 hours apart between the subgroups). Each subject was dosed at least 1 hour apart in the same subgroup. If necessary, dosing of the rest of subjects was delayed pending review of any significant safety issues that may have arisen during the post-dose period involving the first or second subgroups in that cohort. The subsequent cohort was dosed at least 3 weeks after the prior cohort.

Screening Period:

The Screening Visit (Visit 1) occurred up to 21 days prior to the beginning of the active treatment period. After providing informed consent, subjects underwent screening procedures for eligibility.

Treatment Period:

Subjects were admitted to the Clinical Pharmacology Unit (CPU) on Day −1 (Visit 2), and the randomized treatment period began on Day 1 following a 10-hour minimum overnight fast. Subjects were randomly assigned to treatment with CD24Fc or placebo as a single dose. Subjects remained confined until the morning of Day 4.

Follow-Up:

All subjects returned to the CPU on Day 7, Day 14, Day 21, Day 28, and Day 42 (±1 day) for follow-up visits (Visit 3, Visit 4, Visit 5, Visit 6, and Visit 7). Visit 7 was the final visit for all subjects.

Duration of Treatment:

The total study duration for each subject was up to 63 days. Single-dose administration occurred on Day 1.

Number of Subjects:

Planned: 40 subjects

Screened: 224 subjects

Randomized: 40 subjects

Completed: 39 subjects

Discontinued: 1 subject

Diagnosis and Main Criteria for Inclusion:

The population for this study was healthy males and females between the ages of 18 and 55 years, inclusive, with a body mass index between 18 kg/m$^2$ and 30 kg/m$^2$, inclusive.

Investigational Product and Comparator Information:

CD24Fc: single dose of 10 mg, 30 mg, 60 mg, 120 mg, or 240 mg administered via IV infusion; lot number: 09MM- 036. CD24Fc was a fully humanized fusion protein consisting of the mature sequence of human CD24 and the fragment crystallizable region of human immunoglobulin G1 (IgG1Fc). CD24Fc was supplied as a sterile, clear, colorless, preservative-free, aqueous solution for IV administration. CD24Fc was formulated as single dose injection solution, at a concentration of 10 mg/mL and a pH of 7.2. Each CD24Fc vial contained 160 mg of CD24Fc, 5.3 mg of sodium chloride, 32.6 mg of sodium phosphate dibasic heptahydrate, and 140 mg of sodium phosphate monobasic monohydrate in 16 mL±0.2 mL of CD24Fc. CD24Fc was supplied in clear borosilicate glass vials with chlorobutyl rubber stoppers and aluminum flip-off seals.

Matching placebo (0.9% sodium chloride, saline) administered via IV infusion; lot numbers: P296855, P311852, P300715, P315952.

The intent-to-treat (ITT) Population consisted of all subjects who received at least 1 dose of the study drug. The ITT Population was the primary analysis population for subject information and safety evaluation.

Clinical laboratory evaluations (chemistry, hematology, and urinalysis) were summarized by treatment and visit. Change from baseline was also summarized. Vital signs (blood pressure, heart rate, respiratory rate, and temperature) were summarized by treatment and time point. Change from baseline was also summarized. All physical examination data were listed. Electrocardiogram parameters and the change from baseline were summarized. Overall interpretations were listed. Fasting LDL-C and high density lipoprotein cholesterol were obtained on Day −1, Day 7, and Day 42 for Cohort 1 (CD24Fc 10 mg group). Beginning with Cohort 2 (Cd24Fc 30 mg group), this lipid sampling was expanded to include Day 14.

Example 4

CD24 Pharmacokinetics in Humans

This example shows an analysis of the pharmacokinetics of a CD24 protein in humans.

Plasma CD24Fc Concentration

Figure 5:
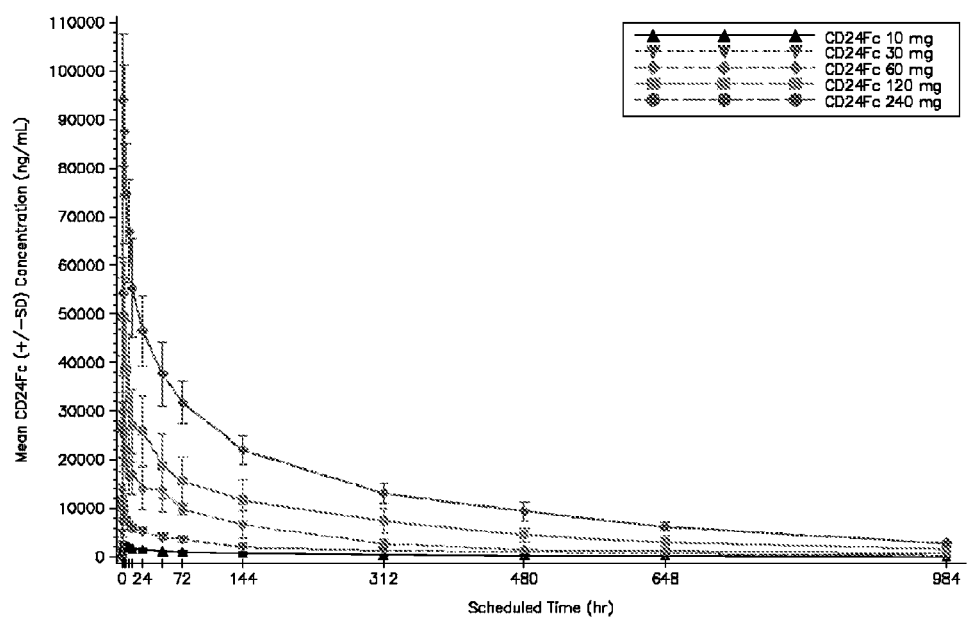
FIG. 5 shows a plot of mean plasma CD24Fc concentration (±SD) by treatment for a PK Evaluable Population in human subjects. PK=pharmacokinetic; SD=standard deviation.

As shown in FIG. 5, the mean plasma concentration of CD24Fc increased proportionally to the dose of CD24Fc administered. For all dose groups except 120 mg, the maximum mean plasma concentration of CD24Fc was reached at 1 hour post-dose. The maximum mean plasma concentration of CD24Fc for the 120 mg group was reached at 2 hours post-dose. By Day 42 (984 hours), the mean plasma concentration of CD24Fc for all groups had decreased to between 2% and 4% of the maximum mean plasma concentration.

Table 3 summarizes the plasma CD24Fc PK parameters by treatment for the PK Evaluable Population.

TABLE 3

Summary of Plasma CD24Fc Pharmacokinetic Parameters by Treatment - PK Evaluable Population

| Parameter Statistic | CD24Fc 10 mg (N = 6) | CD24Fc 30 mg (N = 6) | CD24Fc 60 mg (N = 6) | CD24Fc 120 mg (N = 6) | CD24Fc 240 mg (N = 6) |
|---|---|---|---|---|---|
| $C_{max}$ (ng/mL) | | | | | |
| n | 6 | 6 | 6 | 6 | 6 |
| Mean (SD) | 2495 (576) | 9735 (1715) | 30 083 (7179) | 52 435 (9910) | 95 865 (10 734) |
| CV % | 23.1 | 17.6 | 23.9 | 18.9 | 11.2 |
| Median | 2371 | 9218 | 29 026 | 50 401 | 93 206 |
| Min, Max | 1,967, 3,390 | 8,583, 13,086 | 22,557, 42,628 | 40,434, 65,704 | 81,296, 110,110 |
| Geometric mean | 2,442 | 9,625 | 29,424 | 51,666 | 95,365 |
| Geometric CV % | 22.8 | 16.1 | 23.0 | 19.0 | 11.2 |
| $AUC_{0-42\,d}$ (ng * hr/mL) | | | | | |
| n | 6 | 6 | 6 | 6 | 6 |
| Mean (SD) | 423,061 (99,615) | 1,282,430 (88,798) | 3,226,255 (702,862) | 6,541,501 (2,190,944) | 12,704,705 (1,918,596) |
| CV % | 23.5 | 6.9 | 21.8 | 33.5 | 15.1 |
| Median | 434,043 | 1,302,719 | 3,124,933 | 5,785,142 | 12,563,426 |
| Min, Max | 291,020, 528,079 | 1,175,733, 1,403,024 | 2,487,550, 4,139,748 | 4,485,193, 9,415,266 | 10,466,635, 15,693,606 |
| Geometric mean | 412,795 | 1,279,851 | 3,163,252 | 6,249,552 | 12,586,731 |
| Geometric CV % | 25.0 | 7.0 | 22.0 | 33.8 | 15.0 |
| $AUC_{0-inf}$ (ng * hr/mL) | | | | | |
| n | 6 | 6 | 6 | 6 | 6 |
| Mean (SD) | 462,260 (116,040) | 1,434,464 (131,316) | 3,497,196 (705,653) | 7,198,196 (2,458,320) | 13,861,796 (1,962,780) |
| CV % | 25.1 | 9.2 | 20.2 | 34.2 | 14.2 |
| Median | 470,426 | 1,422,205 | 3,519,732 | 6,463,665 | 13,713,034 |
| Min, Max | 310,956, 596,599 | 1,281,715, 1,650,503 | 2,703,655, 4,309,023 | 4,910,640, 10,479,940 | 11,822,988, 17,175,236 |
| Geometric mean | 449,583 | 1,429,578 | 3,437,036 | 6,862,129 | 13,750,972 |
| Geometric CV % | 26.7 | 9.0 | 20.7 | 34.6 | 13.8 |

TABLE 3-continued

Summary of Plasma CD24Fc Pharmacokinetic Parameters by Treatment - PK Evaluable Population

| Parameter Statistic | CD24Fc 10 mg (N = 6) | CD24Fc 30 mg (N = 6) | CD24Fc 60 mg (N = 6) | CD24Fc 120 mg (N = 6) | CD24Fc 240 mg (N = 6) |
|---|---|---|---|---|---|
| $T_{max}$ (hr) | | | | | |
| n | 6 | 6 | 6 | 6 | 6 |
| Mean (SD) | 1.15 (0.42) | 1.17 (0.41) | 1.01 (0.01) | 1.34 (0.51) | 1.33 (0.52) |
| CV % | 36.1 | 35.0 | 1.2 | 38.0 | 38.7 |
| Median | 1.00 | 1.00 | 1.00 | 1.03 | 1.00 |
| Min, Max | 0.92, 2.00 | 1.00, 2.00 | 1.00, 1.03 | 1.00, 2.00 | 1.00, 2.00 |
| $t_{1/2}$ (hr) | | | | | |
| n | 6 | 6 | 6 | 6 | 6 |
| Mean (SD) | 280.83 (22.37) | 327.10 (41.32) | 279.82 (65.59) | 286.45 (23.38) | 285.33 (24.33) |
| CV % | 8.0 | 12.6 | 23.4 | 8.2 | 8.5 |
| Median | 279.61 | 317.23 | 264.69 | 290.76 | 287.74 |
| Min, Max | 258.87, 321.26 | 289.82, 394.24 | 210.18, 362.46 | 243.89, 309.26 | 249.24, 322.26 |
| AUCextr (%) | | | | | |
| n | 6 | 6 | 6 | 6 | 6 |
| Mean (SD) | 7.61 (2.14) | 10.44 (2.94) | 7.88 (4.26) | 8.92 (1.94) | 8.46 (1.99) |
| CV % | 28.1 | 28.2 | 54.0 | 21.8 | 23.5 |
| Median | 7.16 | 10.01 | 6.35 | 9.27 | 8.45 |
| Min, Max | 5.46, 11.47 | 7.10, 15.05 | 3.92, 14.48 | 5.49, 10.99 | 5.56, 11.50 |
| CL (L/hr) | | | | | |
| n | 6 | 6 | 6 | 6 | 6 |
| Mean (SD) | 0.0229 (0.0061) | 0.0211 (0.0019) | 0.0178 (0.0036) | 0.0183 (0.0058) | 0.0176 (0.0023) |
| CV % | 26.7 | 8.8 | 20.5 | 31.7 | 13.3 |
| Median | 0.0216 | 0.0211 | 0.0173 | 0.0191 | 0.0175 |
| Min, Max | 0.0168, 0.0322 | 0.0182, 0.0234 | 0.0139, 0.0222 | 0.0115, 0.0244 | 0.0140, 0.0203 |
| Vd (L) | | | | | |
| n | 6 | 6 | 6 | 6 | 6 |
| Mean (SD) | 9.153 (1.943) | 9.867 (0.804) | 7.289 (2.592) | 7.491 (2.202) | 7.276 (1.426) |
| CV % | 21.2 | 8.1 | 35.6 | 29.4 | 19.6 |
| Median | 8.507 | 10.007 | 7.486 | 7.691 | 7.151 |
| Min, Max | 7.326, 12.010 | 8.771, 10.958 | 4.222, 11.139 | 4.933, 9.974 | 5.814, 9.438 |

$AUC_{0-42\,d}$ = area under the concentration-time curve from time 0 to 42 days;
$AUC_{0-inf}$ = area under the concentration-time curve extrapolated from time 0 to infinity;
$AUC_{extr}$ = percentage of $AUC_{0-inf}$ that was due to extrapolation from the time of the last measurable concentration, per subject, to infinity;
CL = total body clearance;
$C_{max}$ = maximum observed plasma drug concentration;
CV % = coefficient of variation;
Min = minimum;
Max = maximum;
SD = standard deviation;
$t_{1/2}$ = terminal elimination half-life;
$T_{max}$ = time of maximum observed plasma drug concentration;
$V_d$ = volume of distribution.

Plasma CD24Fc Dose Proportionality Analysis

Figure 6:
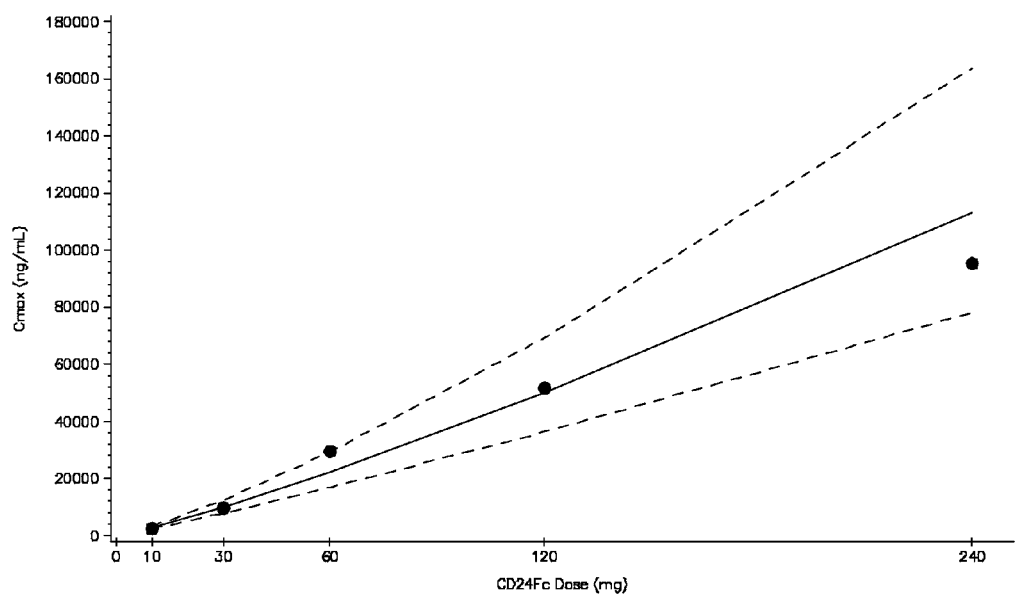
FIG. 6 shows a dose proportionality plot of CD24Fc $C_{max}$ versus dose for a PK Evaluable Population.
Figure 7:
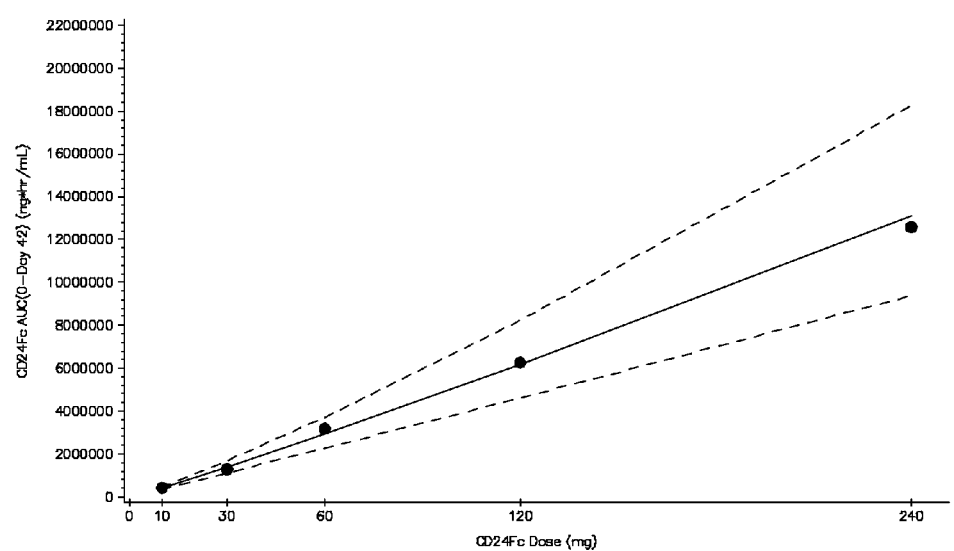
FIG. 7 shows a dose proportionality plot of CD24Fc $AUC_{0-42d}$ versus dose for a PK Evaluable Population.
Figure 8:
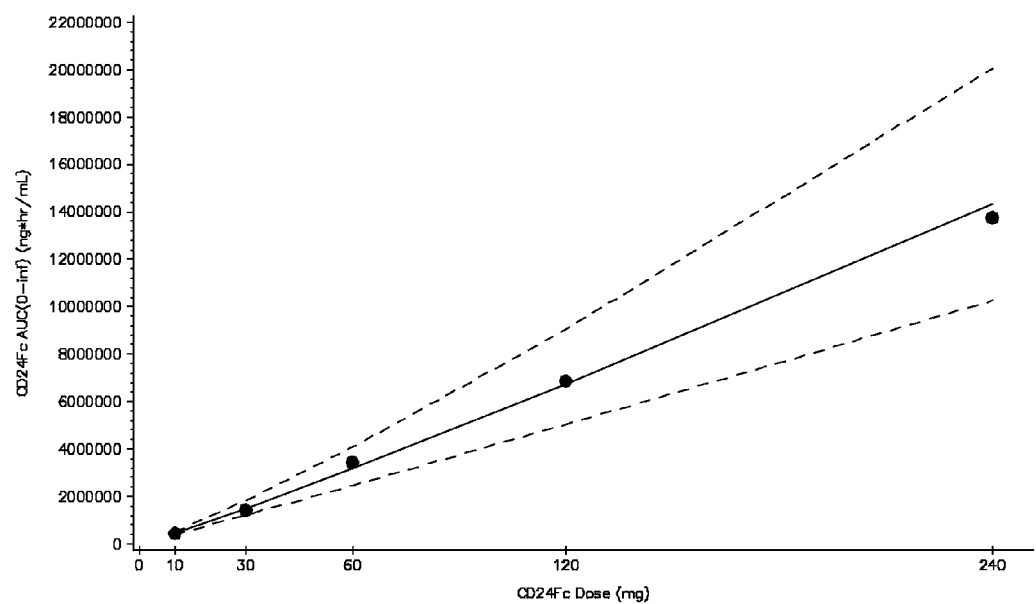
FIG. 8 shows a dose proportionality plot of CD24Fc $AUC_{0-inf}$ versus dose for a PK Evaluable Population.

FIG. 6 shows a dose proportionality plot of CD24Fc $C_{max}$ versus dose for the PK Evaluable Population. FIG. 7 shows a dose proportionality plot of CD24Fc $AUC_{0-42d}$ versus dose for the PK Evaluable Population. FIG. 8 shows a dose proportionality plot of CD24Fc $AUC_{0-inf}$ versus dose for the PK Evaluable Population. Table 4 shows a power analysis of dose proportionality.

TABLE 4

Power Analysis of Dose Proportionality: Plasma CD24Fc Pharmacokinetic Parameters - PK Evaluable Population

| Parameter Statistic | CD24Fc 10 mg (N = 6) | CD24Fc 30 mg (N = 6) | CD24Fc 60 mg (N = 6) | CD24Fc 120 mg (N = 6) | CD24Fc 240 mg (N = 6) | Dose Proportionality Slope Estimate | Standard Error | 90% CI |
|---|---|---|---|---|---|---|---|---|
| $C_{max}$ (ng/mL) | | | | | | 1.172 | 0.040 | (1.105, 1.240) |
| Geometric mean | 2,441.8 | 9,624.9 | 29,424.4 | 51,666.4 | 95,364.9 | | | |
| Geometric CV % | 22.8 | 16.1 | 23.0 | 19.0 | 11.2 | | | |
| $AUC_{0-42\,d}$ (ng * hr/mL) | | | | | | 1.088 | 0.036 | (1.027, 1.148) |
| Geometric mean | 412,794.8 | 1,279,850.8 | 3,163,251.7 | 6,249,551.9 | 12,586,731.3 | | | |
| Geometric CV % | 25.0 | 7.0 | 22.0 | 33.8 | 15.0 | | | |

TABLE 4-continued

Power Analysis of Dose Proportionality: Plasma CD24Fc Pharmacokinetic Parameters - PK Evaluable Population

| Parameter Statistic | CD24Fc 10 mg (N = 6) | CD24Fc 30 mg (N = 6) | CD24Fc 60 mg (N = 6) | CD24Fc 120 mg (N = 6) | CD24Fc 240 mg (N = 6) | Dose Proportionality | | |
|---|---|---|---|---|---|---|---|---|
| | | | | | | Slope Estimate | Standard Error | 90% CI |
| $AUC_{0\text{-}inf}$ (ng * hr/mL) | | | | | | 1.087 | 0.036 | (1.026, 1.148) |
| Geometric mean | 449,583.5 | 1,429,577.5 | 3,437,035.6 | 6,862,128.7 | 13,750,972.4 | | | |
| Geometric CV % | 26.7 | 9.0 | 20.7 | 34.6 | 13.8 | | | |

Geometric CV % = 100 * sqrt(exp($SD^2$) – 1), where SD was the standard deviation of the log-transformed data. The power model was fitted by restricted maximum likelihood, regressing the log-transformed PK parameter on log transformed dose. Both the intercept and slope were fitted as fixed effects. Dose proportionality was not rejected if the 90% CI lies within (0.8, 1.25).
$AUC_{0\text{-}42\ d}$ = area under the concentration-time curve from time 0 to 42 days;
$AUC_{0\text{-}inf}$ = area under the concentration-time curve extrapolated from time 0 to infinity;
CI = confidence interval;
$C_{max}$ = maximum observed plasma drug concentration;
CV % = coefficient of variation;
PK = pharmacokinetic;
SD = standard deviation.

The $C_{max}$ slope estimate was 1.172 with a 90% CI of 1.105 to 1.240. The $AUC_{0\text{-}42d}$ slope estimate was 1.088 with a 90% CI of 1.027 to 1.148. The $AUC_{0\text{-}inf}$ slope estimate was 1.087 with a 90% CI of 1.026 to 1.1.

Pharmacokinetic Conclusions

The $C_{max}$ and AUCs of plasma CD24Fc increased proportionally to the doses administered in mouse, monkey and human. The plasma CD24Fc reached $T_{max}$ between 1.01 and 1.34 hours. The $t_{1/2}$ of plasma CD24Fc ranged between 280.83 and 327.10 hours.

The invention claimed is:

1. A method of reducing low-density lipoprotein (LDL) cholesterol (LDL-C) levels in a human subject in need thereof, comprising administering a CD24 protein to the subject, wherein the CD24 protein comprises: (a) a mature human CD24 polypeptide comprising the sequence set forth in SEQ ID NO: 1 or 2; and, (b) a Fc region of a human IgG protein; and, wherein the Fc region is fused at the C-terminus of the CD24 protein.

2. The method of claim 1, wherein the subject has an elevated LDL-C.

3. The method of claim 2, wherein the subject has a LDL-C greater than or equal to 75 mg/dL.

4. The method of claim 2, wherein the subject has a LDL-C of greater than or equal to 70 mg/dL or 190 mg/dL.

5. The method of claim 1, wherein the subject has been previously treated with another LDL-C-lowering drug.

6. The method of claim 5, wherein the other LDL-C-lowering drug is a statin.

7. The method of claim 5, wherein the other LDL-C-lowering drug is an antagonist of PCSK9.

8. The method of claim 1, wherein the CD24 protein is soluble.

9. The method of claim 1, wherein the CD24 protein is glycosylated.

10. The method of claim 1, wherein the Fc region comprises a hinge region and CH2 and CH3 domains of the human IgG protein.

11. The method of claim 10, wherein the human IgG protein is selected from the group consisting of IgG1, IgG2, IgG3, and IgG4.

12. The method of claim 11, wherein the CD24 protein comprises the sequence set forth in SEQ ID NO: 6, ii, or 12.

13. The method of claim 1, wherein the CD24 protein is produced using a eukaryotic protein expression system.

14. The method of claim 13, wherein the expression system comprises a vector contained in a Chinese Hamster Ovary cell line or a replication-defective retroviral vector.

15. The method of claim 14, wherein the replication-defective retroviral vector is stably integrated into the genome of a eukaryotic cell.

16. A method of treating atherosclerosis in a human subject in need thereof, comprising administering a CD24 protein to the subject, wherein the amino acid sequence of the CD24 protein consists of SEQ ID NO: 6, 11, or 12.

17. A method of lowering the risk of atherosclerotic cardiovascular disease in a human subject in need thereof, comprising administering a CD24 protein to the subject, wherein the amino acid sequence of the CD24 protein consists of SEQ ID NO: 6, 11, or 12.

18. The method of claim 12, wherein the amino acid sequence of the CD24 protein consists of the sequence set forth in SEQ ID NO: 6, ii or 12.

19. The method of claim 16, wherein the CD24 protein is soluble.

20. The method of claim 17, wherein the CD24 protein is soluble.

21. A method of reducing LDL-C levels in a human subject in need thereof, comprising administering to the subject a CD24 protein consisting of the sequence set forth in SEQ ID NO: 6.

* * * * *

SEQUENCE LISTING

<160> NUMBER OF SEQ ID NOS: 12

<210> SEQ ID NO 1
<211> LENGTH: 31
<212> TYPE: PRT
<213> ORGANISM: Homo sapiens
<220> FEATURE:
<221> NAME/KEY: X
<222> LOCATION: (31)..(31)
<223> OTHER INFORMATION: Valine or Alanine

<400> SEQUENCE: 1

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Xaa
            20                  25                  30

<210> SEQ ID NO 2
<211> LENGTH: 30
<212> TYPE: PRT
<213> ORGANISM: Homo sapiens

<400> SEQUENCE: 2

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys
            20                  25                  30

<210> SEQ ID NO 3
<211> LENGTH: 27
<212> TYPE: PRT
<213> ORGANISM: Mus musculus

<400> SEQUENCE: 3

```
Asn Gln Thr Ser Val Ala Pro Phe Pro Gly Asn Gln Asn Ile Ser Ala
1               5                   10                  15

Ser Pro Asn Pro Thr Asn Ala Thr Thr Arg Gly
            20                  25
```

<210> SEQ ID NO 4
<211> LENGTH: 26
<212> TYPE: PRT
<213> ORGANISM: Homo sapiens

<400> SEQUENCE: 4

```
Met Gly Arg Ala Met Val Ala Arg Leu Gly Leu Gly Leu Leu Leu Leu
1               5                   10                  15

Ala Leu Leu Leu Pro Thr Gln Ile Tyr Ser
            20                  25
```

<210> SEQ ID NO 5
<211> LENGTH: 287
<212> TYPE: PRT
<213> ORGANISM: Artificial
<220> FEATURE:
<223> OTHER INFORMATION: Fusion protein

<400> SEQUENCE: 5

```
Met Gly Arg Ala Met Val Ala Arg Leu Gly Leu Gly Leu Leu Leu Leu
1               5                   10                  15

Ala Leu Leu Leu Pro Thr Gln Ile Tyr Ser Ser Glu Thr Thr Thr Gly
            20                  25                  30

Thr Ser Ser Asn Ser Ser Gln Ser Thr Ser Asn Ser Gly Leu Ala Pro
            35                  40                  45

Asn Pro Thr Asn Ala Thr Thr Lys Pro Lys Ser Cys Asp Lys Thr His
50                  55                  60

Thr Cys Pro Pro Cys Pro Ala Pro Glu Leu Leu Gly Gly Pro Ser Val
65                  70                  75                  80

Phe Leu Phe Pro Pro Lys Pro Lys Asp Thr Leu Met Ile Ser Arg Thr
                85                  90                  95

Pro Glu Val Thr Cys Val Val Val Asp Val Ser His Glu Asp Pro Glu
                100                 105                 110

Val Lys Phe Asn Trp Tyr Val Asp Gly Val Glu Val His Asn Ala Lys
            115                 120                 125

Thr Lys Pro Arg Glu Glu Gln Tyr Asn Ser Thr Tyr Arg Val Val Ser
130                 135                 140

Val Leu Thr Val Leu His Gln Asp Trp Leu Asn Gly Lys Glu Tyr Lys
145                 150                 155                 160

Cys Lys Val Ser Asn Lys Ala Leu Pro Ala Pro Ile Glu Lys Thr Ile
                165                 170                 175

Ser Lys Ala Lys Gly Gln Pro Arg Glu Pro Gln Val Tyr Thr Leu Pro
            180                 185                 190

Pro Ser Arg Asp Glu Leu Thr Lys Asn Gln Val Ser Leu Thr Cys Leu
            195                 200                 205

Val Lys Gly Phe Tyr Pro Ser Asp Ile Ala Val Glu Trp Glu Ser Asn
            210                 215                 220

Gly Gln Pro Glu Asn Asn Tyr Lys Thr Thr Pro Pro Val Leu Asp Ser
225                 230                 235                 240

Asp Gly Ser Phe Phe Leu Tyr Ser Lys Leu Thr Val Asp Lys Ser Arg
                245                 250                 255
```

Trp Gln Gln Gly Asn Val Phe Ser Cys Ser Val Met His Glu Ala Leu
                260                 265                 270

His Asn His Tyr Thr Gln Lys Ser Leu Ser Leu Ser Pro Gly Lys
        275                 280                 285

<210> SEQ ID NO 6
<211> LENGTH: 261
<212> TYPE: PRT
<213> ORGANISM: Artificial
<220> FEATURE:
<223> OTHER INFORMATION: Fusion protein

<400> SEQUENCE: 6

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Pro Lys
            20                  25                  30

Ser Cys Asp Lys Thr His Thr Cys Pro Pro Cys Pro Ala Pro Glu Leu
        35                  40                  45

Leu Gly Gly Pro Ser Val Phe Leu Phe Pro Pro Lys Pro Lys Asp Thr
    50                  55                  60

Leu Met Ile Ser Arg Thr Pro Glu Val Thr Cys Val Val Val Asp Val
65                  70                  75                  80

Ser His Glu Asp Pro Glu Val Lys Phe Asn Trp Tyr Val Asp Gly Val
                85                  90                  95

Glu Val His Asn Ala Lys Thr Lys Pro Arg Glu Glu Gln Tyr Asn Ser
            100                 105                 110

Thr Tyr Arg Val Val Ser Val Leu Thr Val Leu His Gln Asp Trp Leu
        115                 120                 125

Asn Gly Lys Glu Tyr Lys Cys Lys Val Ser Asn Lys Ala Leu Pro Ala
    130                 135                 140

Pro Ile Glu Lys Thr Ile Ser Lys Ala Lys Gly Gln Pro Arg Glu Pro
145                 150                 155                 160

Gln Val Tyr Thr Leu Pro Pro Ser Arg Asp Glu Leu Thr Lys Asn Gln
                165                 170                 175

Val Ser Leu Thr Cys Leu Val Lys Gly Phe Tyr Pro Ser Asp Ile Ala
            180                 185                 190

Val Glu Trp Glu Ser Asn Gly Gln Pro Glu Asn Asn Tyr Lys Thr Thr
        195                 200                 205

Pro Pro Val Leu Asp Ser Asp Gly Ser Phe Phe Leu Tyr Ser Lys Leu
    210                 215                 220

Thr Val Asp Lys Ser Arg Trp Gln Gln Gly Asn Val Phe Ser Cys Ser
225                 230                 235                 240

Val Met His Glu Ala Leu His Asn His Tyr Thr Gln Lys Ser Leu Ser
                245                 250                 255

Leu Ser Pro Gly Lys
            260

<210> SEQ ID NO 7
<211> LENGTH: 231
<212> TYPE: PRT
<213> ORGANISM: Homo sapiens

<400> SEQUENCE: 7

Pro Lys Ser Cys Asp Lys Thr His Thr Cys Pro Pro Cys Pro Ala Pro
1               5                   10                  15

Glu Leu Leu Gly Gly Pro Ser Val Phe Leu Phe Pro Pro Lys Pro Lys

```
                20                  25                  30
Asp Thr Leu Met Ile Ser Arg Thr Pro Glu Val Thr Cys Val Val
        35                  40                  45
Asp Val Ser His Glu Asp Pro Glu Val Lys Phe Asn Trp Tyr Val Asp
    50                  55                  60
Gly Val Glu Val His Asn Ala Lys Thr Lys Pro Arg Glu Glu Gln Tyr
65                  70                  75                  80
Asn Ser Thr Tyr Arg Val Val Ser Val Leu Thr Val Leu His Gln Asp
                85                  90                  95
Trp Leu Asn Gly Lys Glu Tyr Lys Cys Lys Val Ser Asn Lys Ala Leu
            100                 105                 110
Pro Ala Pro Ile Glu Lys Thr Ile Ser Lys Ala Lys Gly Gln Pro Arg
        115                 120                 125
Glu Pro Gln Val Tyr Thr Leu Pro Pro Ser Arg Asp Glu Leu Thr Lys
    130                 135                 140
Asn Gln Val Ser Leu Thr Cys Leu Val Lys Gly Phe Tyr Pro Ser Asp
145                 150                 155                 160
Ile Ala Val Glu Trp Glu Ser Asn Gly Gln Pro Glu Asn Asn Tyr Lys
                165                 170                 175
Thr Thr Pro Pro Val Leu Asp Ser Asp Gly Ser Phe Phe Leu Tyr Ser
            180                 185                 190
Lys Leu Thr Val Asp Lys Ser Arg Trp Gln Gln Gly Asn Val Phe Ser
        195                 200                 205
Cys Ser Val Met His Glu Ala Leu His Asn His Tyr Thr Gln Lys Ser
    210                 215                 220
Leu Ser Leu Ser Pro Gly Lys
225                 230

<210> SEQ ID NO 8
<211> LENGTH: 288
<212> TYPE: PRT
<213> ORGANISM: Artificial
<220> FEATURE:
<223> OTHER INFORMATION: Fusion protein

<400> SEQUENCE: 8

Met Gly Arg Ala Met Val Ala Arg Leu Gly Leu Gly Leu Leu Leu Leu
1               5                   10                  15
Ala Leu Leu Leu Pro Thr Gln Ile Tyr Ser Ser Glu Thr Thr Thr Gly
                20                  25                  30
Thr Ser Ser Asn Ser Ser Gln Ser Thr Ser Asn Ser Gly Leu Ala Pro
            35                  40                  45
Asn Pro Thr Asn Ala Thr Thr Lys Val Pro Lys Ser Cys Asp Lys Thr
    50                  55                  60
His Thr Cys Pro Pro Cys Pro Ala Pro Glu Leu Leu Gly Gly Pro Ser
65                  70                  75                  80
Val Phe Leu Phe Pro Pro Lys Pro Lys Asp Thr Leu Met Ile Ser Arg
                85                  90                  95
Thr Pro Glu Val Thr Cys Val Val Val Asp Val Ser His Glu Asp Pro
            100                 105                 110
Glu Val Lys Phe Asn Trp Tyr Val Asp Gly Val Glu Val His Asn Ala
        115                 120                 125
Lys Thr Lys Pro Arg Glu Glu Gln Tyr Asn Ser Thr Tyr Arg Val Val
    130                 135                 140
Ser Val Leu Thr Val Leu His Gln Asp Trp Leu Asn Gly Lys Glu Tyr
```

```
            145                 150                 155                 160
        Lys Cys Lys Val Ser Asn Lys Ala Leu Pro Ala Pro Ile Glu Lys Thr
                        165                 170                 175

Ile Ser Lys Ala Lys Gly Gln Pro Arg Glu Pro Gln Val Tyr Thr Leu
                        180                 185                 190

Pro Pro Ser Arg Asp Glu Leu Thr Lys Asn Gln Val Ser Leu Thr Cys
                        195                 200                 205

Leu Val Lys Gly Phe Tyr Pro Ser Asp Ile Ala Val Glu Trp Glu Ser
                        210                 215                 220

Asn Gly Gln Pro Glu Asn Asn Tyr Lys Thr Thr Pro Pro Val Leu Asp
        225                 230                 235                 240

Ser Asp Gly Ser Phe Phe Leu Tyr Ser Lys Leu Thr Val Asp Lys Ser
                        245                 250                 255

Arg Trp Gln Gln Gly Asn Val Phe Ser Cys Ser Val Met His Glu Ala
                        260                 265                 270

Leu His Asn His Tyr Thr Gln Lys Ser Leu Ser Leu Ser Pro Gly Lys
                        275                 280                 285

<210> SEQ ID NO 9
<211> LENGTH: 288
<212> TYPE: PRT
<213> ORGANISM: Artificial
<220> FEATURE:
<223> OTHER INFORMATION: Fusion protein

<400> SEQUENCE: 9

Met Gly Arg Ala Met Val Ala Arg Leu Gly Leu Gly Leu Leu Leu Leu
        1               5                   10                  15

Ala Leu Leu Leu Pro Thr Gln Ile Tyr Ser Ser Glu Thr Thr Thr Gly
                        20                  25                  30

Thr Ser Ser Asn Ser Ser Gln Ser Thr Ser Asn Ser Gly Leu Ala Pro
                        35                  40                  45

Asn Pro Thr Asn Ala Thr Thr Lys Ala Pro Lys Ser Cys Asp Lys Thr
                        50                  55                  60

His Thr Cys Pro Pro Cys Pro Ala Pro Glu Leu Leu Gly Gly Pro Ser
        65                  70                  75                  80

Val Phe Leu Phe Pro Pro Lys Pro Lys Asp Thr Leu Met Ile Ser Arg
                        85                  90                  95

Thr Pro Glu Val Thr Cys Val Val Val Asp Val Ser His Glu Asp Pro
                        100                 105                 110

Glu Val Lys Phe Asn Trp Tyr Val Asp Gly Val Glu Val His Asn Ala
                        115                 120                 125

Lys Thr Lys Pro Arg Glu Glu Gln Tyr Asn Ser Thr Tyr Arg Val Val
                        130                 135                 140

Ser Val Leu Thr Val Leu His Gln Asp Trp Leu Asn Gly Lys Glu Tyr
        145                 150                 155                 160

Lys Cys Lys Val Ser Asn Lys Ala Leu Pro Ala Pro Ile Glu Lys Thr
                        165                 170                 175

Ile Ser Lys Ala Lys Gly Gln Pro Arg Glu Pro Gln Val Tyr Thr Leu
                        180                 185                 190

Pro Pro Ser Arg Asp Glu Leu Thr Lys Asn Gln Val Ser Leu Thr Cys
                        195                 200                 205

Leu Val Lys Gly Phe Tyr Pro Ser Asp Ile Ala Val Glu Trp Glu Ser
                        210                 215                 220

Asn Gly Gln Pro Glu Asn Asn Tyr Lys Thr Thr Pro Pro Val Leu Asp
```

```
                225                 230                 235                 240
Ser Asp Gly Ser Phe Phe Leu Tyr Ser Lys Leu Thr Val Asp Lys Ser
                    245                 250                 255

Arg Trp Gln Gln Gly Asn Val Phe Ser Cys Ser Val Met His Glu Ala
                260                 265                 270

Leu His Asn His Tyr Thr Gln Lys Ser Leu Ser Leu Ser Pro Gly Lys
                275                 280                 285

<210> SEQ ID NO 10
<211> LENGTH: 29
<212> TYPE: PRT
<213> ORGANISM: Macaca fascicularis

<400> SEQUENCE: 10

Thr Val Thr Thr Ser Ala Pro Leu Ser Ser Asn Ser Pro Gln Asn Thr
1               5                   10                  15

Ser Thr Thr Pro Asn Pro Ala Asn Thr Thr Lys Ala
            20                  25

<210> SEQ ID NO 11
<211> LENGTH: 262
<212> TYPE: PRT
<213> ORGANISM: Artificial
<220> FEATURE:
<223> OTHER INFORMATION: Fusion protein

<400> SEQUENCE: 11

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Val Pro
            20                  25                  30

Lys Ser Cys Asp Lys Thr His Thr Cys Pro Pro Cys Pro Ala Pro Glu
        35                  40                  45

Leu Leu Gly Gly Pro Ser Val Phe Leu Phe Pro Pro Lys Pro Lys Asp
    50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
                85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
        115                 120                 125

Leu Asn Gly Lys Glu Tyr Lys Cys Lys Val Ser Asn Lys Ala Leu Pro
    130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
        195                 200                 205

Thr Pro Pro Val Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240
```

```
Ser Val Met His Glu Ala Leu His Asn His Tyr Thr Gln Lys Ser Leu
            245                 250                 255

Ser Leu Ser Pro Gly Lys
            260

<210> SEQ ID NO 12
<211> LENGTH: 262
<212> TYPE: PRT
<213> ORGANISM: Artificial
<220> FEATURE:
<223> OTHER INFORMATION: Fusion protein

<400> SEQUENCE: 12

Ser Glu Thr Thr Thr Gly Thr Ser Ser Asn Ser Ser Gln Ser Thr Ser
1               5                   10                  15

Asn Ser Gly Leu Ala Pro Asn Pro Thr Asn Ala Thr Thr Lys Ala Pro
            20                  25                  30

Lys Ser Cys Asp Lys Thr His Thr Cys Pro Pro Cys Pro Ala Pro Glu
            35                  40                  45

Leu Leu Gly Gly Pro Ser Val Phe Leu Phe Pro Pro Lys Pro Lys Asp
50                  55                  60

Thr Leu Met Ile Ser Arg Thr Pro Glu Val Thr Cys Val Val Val Asp
65                  70                  75                  80

Val Ser His Glu Asp Pro Glu Val Lys Phe Asn Trp Tyr Val Asp Gly
            85                  90                  95

Val Glu Val His Asn Ala Lys Thr Lys Pro Arg Glu Glu Gln Tyr Asn
            100                 105                 110

Ser Thr Tyr Arg Val Val Ser Val Leu Thr Val Leu His Gln Asp Trp
            115                 120                 125

Leu Asn Gly Lys Glu Tyr Lys Cys Lys Val Ser Asn Lys Ala Leu Pro
            130                 135                 140

Ala Pro Ile Glu Lys Thr Ile Ser Lys Ala Lys Gly Gln Pro Arg Glu
145                 150                 155                 160

Pro Gln Val Tyr Thr Leu Pro Pro Ser Arg Asp Glu Leu Thr Lys Asn
                165                 170                 175

Gln Val Ser Leu Thr Cys Leu Val Lys Gly Phe Tyr Pro Ser Asp Ile
            180                 185                 190

Ala Val Glu Trp Glu Ser Asn Gly Gln Pro Glu Asn Asn Tyr Lys Thr
            195                 200                 205

Thr Pro Pro Val Leu Asp Ser Asp Gly Ser Phe Phe Leu Tyr Ser Lys
    210                 215                 220

Leu Thr Val Asp Lys Ser Arg Trp Gln Gln Gly Asn Val Phe Ser Cys
225                 230                 235                 240

Ser Val Met His Glu Ala Leu His Asn His Tyr Thr Gln Lys Ser Leu
            245                 250                 255

Ser Leu Ser Pro Gly Lys
            260
```